United States Patent
DiMauro et al.

(10) Patent No.: US 10,064,417 B2
(45) Date of Patent: Sep. 4, 2018

(54) MILK FILTRATION DEVICES AND METHODS FOR FILTERING

(71) Applicant: Janssen Pharmaceutica NV, Beerse (BE)

(72) Inventors: Thomas M DiMauro, Southboro, MA (US); Kevin Wildenhaus, Plymouth, MI (US)

(73) Assignee: Janssen Pharmaceutica NV, Beerse (BE)

(*) Notice: Subject to any disclaimer, the term of this patent is extended or adjusted under 35 U.S.C. 154(b) by 0 days.

(21) Appl. No.: 15/274,264

(22) Filed: Sep. 23, 2016

(65) Prior Publication Data

US 2017/0164630 A1 Jun. 15, 2017

Related U.S. Application Data

(60) Provisional application No. 62/265,450, filed on Dec. 10, 2015, provisional application No. 62/293,378, filed on Feb. 10, 2016.

(51) Int. Cl.
| | |
|---|---|
| *A23L 1/015* | (2006.01) |
| *A23C 7/04* | (2006.01) |
| *A61M 1/06* | (2006.01) |
| *A23C 9/142* | (2006.01) |
| *A23C 9/20* | (2006.01) |

(52) U.S. Cl.
CPC ............. *A23C 7/043* (2013.01); *A23C 9/142* (2013.01); *A23C 9/206* (2013.01); *A61M 1/064* (2014.02)

(58) Field of Classification Search
CPC ......... A23C 7/04; A23C 9/1422; A23C 7/043; A23C 9/142; A23C 9/206; A01J 9/02; A01J 11/06; A61M 1/06
USPC ............ 426/231, 580, 648, 2, 425, 478, 491
See application file for complete search history.

(56) References Cited

U.S. PATENT DOCUMENTS

| | | | |
|---|---|---|---|
| 4,898,735 | A | 2/1990 | Barenholz |
| 5,616,341 | A | 4/1997 | Mayer |
| 5,736,155 | A | 4/1998 | Bally |
| 8,357,117 | B2 | 1/2013 | Sokal |
| 2002/0012727 | A1 | 1/2002 | Oakland |
| 2004/0178162 | A1* | 9/2004 | Zucker-Franklin |
| 2007/0005006 | A1* | 1/2007 | Rosenfeld |
| 2007/0010760 | A1* | 1/2007 | Rosenfeld |
| 2016/0021904 | A1* | 1/2016 | Verdi |

OTHER PUBLICATIONS

Abulateefeh, "Synthesis and Characterization of PLGA Shell Microcapsules Containing Aqueous Cores Prepared by Internal Phase Separation", *AAPS PharmScitech.*, 2015, vol. 17, No. 4. pp. 891-897.
Berle, "Antidepressant Use During Breastfeeding", *Curr. Womens Health Rev.* Feb. 2011;7(1):28-34.

(Continued)

*Primary Examiner* — Helen F Heggestad (57) ABSTRACT

A method of cleaning mother's milk, involving ex vivo contacting mother's milk having an initial concentration of an antidepressant therein with a solid substrate (preferably a porous substrate) adapted to remove the antidepressant from the milk to produce a cleansed milk product having a reduced concentration of the antidepressant.

18 Claims, 8 Drawing Sheets

(56) References Cited

OTHER PUBLICATIONS

Bolze, "HPLC determination of ketamine, norketamine, and dehydronorketamine in plasma with a high-purity reversed-phase sorbent" *Clin. Chem.* 1998, vol. 44,Issue 3, pp. 566-564.

Kazmi, Lysosomal Sequestration (Trapping) of Lipophilic Amine (Cationic Amphiphilic) Drugs in Immortalized Human Hepatocytes (Fa2N-4 Cells), *Drug Metab Dispos.*, Apr. 2013; 41(4): 897-905.).

Klemetsrud, "Studies on pectin-coated liposomes and their interaction with mucin", *Colloids Surfaces B: Biointerfaces* 103 (2013) 158-165.

Lai, "Nanoparticles reveal that human cervicovaginal mucus is riddled with pores larger than viruses", *PNAS*, 107,2, 598-603, 2010.

Li, J. "Study on the Protein Binding of Ketoprofen Using Capillary Electrophoresis Frontal Analysis Compared with Liquid Chromatography Frontal Analysys", *Chromat. Sci.*, 41, Mar. 2003, 137-141.

Mandrioli, HPLC Analysys of the second-generation antidepressant setraline and its maine metabolite N-desmethylsertraline in human plasma, *J. Chromotography B*, vol. 836, Issues 1-2, (2006) pp. 116-119, Elsevier.

Mayer, "Influence of Vesicle Size, Lipid Composition, and Drug-to-Lipid Ratio on the Biological Activity of Liposomal Doxorubicin in Mice", *Cancer Res.*, Nov. 1, 1989, 49,21,5922-30.

Meng, "Fast screening of ketamine in biological samples based on molecularly imprinted photonic hydrogels", *Anal Chim Acta.* , Apr. 10, 2013; 771, pp. 86-94 Epub Feb. 8, 2013, Elsevier B.V.

Ohnishi, "Frontal analysis of drug-plasma lipoprotein binding using capillary electrophoresis", *J. Pharm. Biomed. Anal.*, Jan. 15, 2002, 27(3-4) 607-14.

Orczyk-Pawilowicz, "Lactation Stage Related Expression of Sialylated and Fucosylated Glycotopes of Human Milk α-1-Acid Glycoprotein", *Breastfeed. Med.*, Jun. 2014:9,313-9.

Shibukawa, "High-Performance Capillary Electrophoresis/Frontal Analysys for the Study of Protein Binding of a Basic Drug", *J. Pharm. Sci.*, May 1994, 83(5) 616-9.

Sirgom da Silva, "On-Line Restricted Access Molecularly Imprinted Solid-Phase Extraction of Selective Serotonin Reuptake Inhibitors Directly from Untreated Human Plasma Samples Followed by HPLC-UV Analysis", *J Anal Toxicol* (Oct. 20, 2015).

Soundararajan, "[186Re]Liposomal doxorubicin (Doxil): in vitro stability, pharmacokinetics, imaging and biodistribution in a head and neck squamous cell carcinoma xenograft model", *Nucl. Med. Biol.* Jul. 2009, 36(5) 515-524.

Thirawong, "Improved intestinal absorption of calcitonin by mucoadhesive delivery of novel pectin-liposome nanocomplexes", *J. Controlled Release*, 125 (2008) 236-245.

Yang, "Avidin-biotin immobilization of unilamellar liposomes in gel beads for chromatographic analysis of drug-membrane partitioning,", *J Chromatogr B Biomed Sci Appl.* Apr. 10, 1998;707(1-2):131-41.

Yolken, "Human Milk Mucin Inhibits Rotavirus Replication and Prevents Experimental Gastroenteritis", *J. Clin. Invest.*, 90, Nov. 1992 (1984-1991).

Yulan, "The In Vivo and In Vitro Studies of Drug Milk: Plasma Distribution and Assessing the Risk to Infant", Dept. of Pharmacy National University Singapore, 2005, pp. 1-137.

* cited by examiner

MILK FILTRATION DEVICES AND METHODS FOR FILTERING

CONTINUING DATA

This application claims priority from provisional patent application U.S. Ser. No. 62/265,450, entitled "Milk Filtration Devices and Methods for Filtering" (DiMauro), filed Dec. 10, 2015 and from provisional patent application U.S. Ser. No. 62/293,378, entitled "Milk Filtration Devices and Methods for Filtering" (DiMauro), filed Feb. 10, 2016, the specification of which are incorporated by reference in their entireties.

BACKGROUND

The loving connection between a mother and her baby is a special bonding that can benefit the baby not only in the present, but also well into the future. Bonding brings the mother and child closer together, and this positive attachment can enhance the baby's well-being and later development. Because a healthy bond between the mother and her newborn infant is crucial to the proper development of the child, loving efforts to strengthen that bond are highly valued. Some of the ways in which a healthy mother can show love for her child and promote this bonding is by experiencing joy at her child's smile and by providing appropriate attention to her child's needs.

It has been estimated that over 700,000 mothers are afflicted with postpartum depression (PPD) each year in the United States. PPD is considered to be a major depression, and is characterized by standard depressive features. Typical PPD symptoms include non-responsiveness towards the infant's needs and an absence of joy that is normally associated with healthy parent-child interaction and attachment. Because the first months of life are a critical period for an infant's proper cognitive and emotional development, the lack of attachment and attention towards the infant shown by the PPD mother may cause undesired effects in the child's future behaviors.

During pregnancy, the hormonal balance in the healthy expectant mother is such that she experiences extremely high levels of estrogen throughout her body. These levels of estrogen in the expectant mother may be up to 100 times the normal level. After the birth of the child, the estrogen level in the new mother rapidly decreases over the course of a few days and returns to the normal level of estrogen. Estrogen has been found to be critical to many normal neuronal processes, and has been positively associated with serotonin levels in the brain and brain plasticity. Therefore, and without wishing to be tied to a theory, it is believed that PPD may be caused by an extra-sensitive response in a subset of new mothers to the rapid withdrawal of estrogen from the mother's system.

Antidepressants are often one of the first lines of therapy against PPD. Conventional antidepressants such as tricyclics and selective serotonin reuptake inhibitors (SSRIs) are commonly prescribed for PPD. However, there are many problems associated with the use of these conventional antidepressants for PPD. First, these conventional antidepressants typically alleviate the PPD condition in no more than about 80% of the patients taking them. Second, even when successful, these conventional antidepressants typically take up to 8 weeks be effective. Third, the PPD mother can expect to experience the typical side effects associated with tricyclics and SSRIs. Side effects associated with tricyclics use include dry mouth, dry nose, blurred vision, decreased gastro-intestinal motility and secretion, leading to. Side effects associated with SSRI use include insomnia, weight gain and sexual dysfunction.

In addition, it has been found that virtually all of these conventional antidepressants are found in the mother's milk, and may be transferred to the infant during nursing. There has been little data on the effect of the nursing mother's antidepressant use upon the child's mental development. Rather than demonstrating safety, the literature appears to conclude that the risk to the nursing child posed by the mother's antidepressant use is outweighed by the risks associated with untreated PPD. However, in some cases, the transfer of some particular antidepressants to mother's milk has been so significant that some investigators have concluded that those particular antidepressants should be avoided by nursing mothers.

Sertraline (Zoloft) and paroxetine (Paxil) are the first-line antidepressants for treating PPD (Berle, *Curr. Womens Health Rev.* 2011 February; 7(1):28-34). No long term studies on the effects of these antidepressants on infants who receive their mother's milk.

In human blood, sertraline is 95% bound to a protein called orosomucoid. Sekar, "Pharmacokinetic interaction between darunavir (TMC114), a new protease inhibitor, and the selective serotonin reuptake inhibitors (SSRIs), paroxetine and sertraline", 8th International Congress on Drug Therapy in HIV Infection, Glasgow, UK, 12-16 Nov. 2006. In mother's milk, the orosomucoid concentration is only about 3% that of the mother's plasma concentration. (Orczyk-Pawilowicz, Breastfeed. Med., 2014 June: 9, 313-9). According to a 2005 Hu Yulan dissertation, "The In Vivo and In Vitro Studies of Drug Milk: Plasma Distribution and Assessing The Risk To Infant", sertraline is about 80% bound in mother's milk.

Prior art technology used to analyze the concentration of sertraline in mother's milk appears to use liquid-liquid partitioning to remove sertraline from mother's milk, not solid phase filtering. Attempts have been made to reduce transmission of components by filling the nipple of a nipple shield with an insert, such as a fiber insert, including a microbicide to prevent transmission of disease, such as HIV.

U.S. Pat. No. 8,357,117 (Sokal) discloses a nipple shield adapted to filter breast milk by means of a non-woven material impregnated with an active agent such as sodium dodecyl sulphate (SDS). In some embodiments, Sokal at (7, 25-50) discloses adding to the filter a disc containing a flavoring agent to make the taste of a milk/drug solution more acceptable to the infant.

US Patent Publication US 2007-0010760 (Rosenfeld) discloses filters for filtering contaminants out of breast milk. In some embodiments, Rosenfeld at [0073] discloses the use of cationic and anionic resins that adsorb anions and cations.

SUMMARY

It has been observed that there are a number of commercial filters that can remove sertraline from blood. These filters are often used by law enforcement officials to determine the levels of sertraline in a person's blood. Since blood and mother's milk are both aqueous liquids, it is contemplated that the filters that can remove sertraline from blood can also remove sertraline from mother's milk. One aspect of the present invention includes the use of filtering devices to remove certain components, including sertraline, from mother's milk.

Figure 1A:
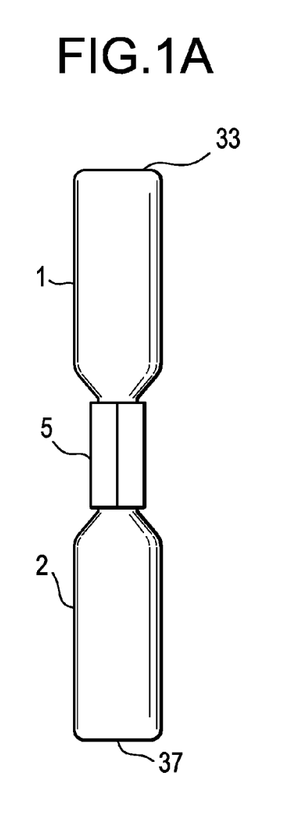
FIGS. 1a and 1b are perspective and cross-sectional views of a fitting that has a filter and attaches to two milk bottles whose open faces attach to the fitting. The expressed milk is contained in one of the bottles from the breast pump and is run downward through the filter. The filtrate is received in the other milk bottle.
Figure 1B:
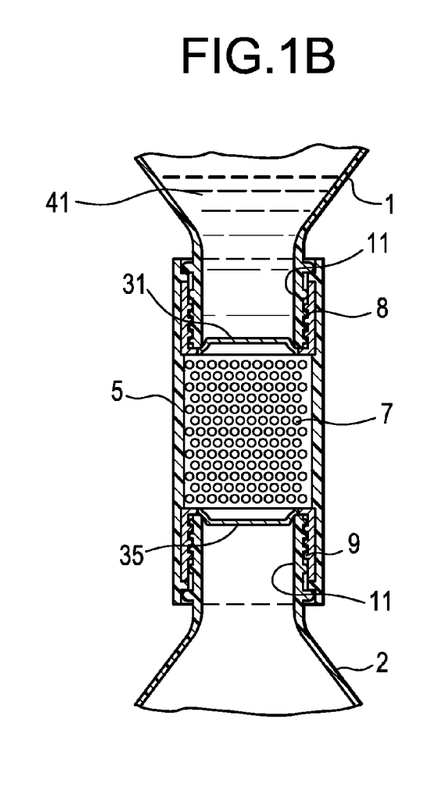

In other aspects, and now referring to FIGS. 1a and 1b, there is provided a method of cleaning mother's milk, including: ex vivo contacting mother's milk having an initial concentration of an antidepressant therein with a solid substrate (preferably a porous substrate) adapted to remove the antidepressant from the milk to produce a cleansed milk product having a reduced concentration of the antidepressant.

DETAILED DESCRIPTION

In some embodiments, treatment of the mother's milk in accordance with the above methods results in a reduction of at least 30% from the initial concentration of the antidepressant in the mother's milk. Preferably, the reduction is at least 75%, more preferably at least 90%, more preferably at least 95%, most preferably at least 99%. As used herein, the term "mother's milk" and "breastmilk" are used synonymously, and refer to milk that is expressed from a human breast. As used below, the term "antidepressant" refers to one or more chemical compounds that acts as an antidepressant in humans, or compounds included in antidepressant drugs that are provided to humans.

Although the present invention discusses and focuses on the filtering of compounds associated with antidepressants from milk, it is understood that the present invention may be used to filter additional compounds from milk. In some embodiments, the filter is adapted to remove phytoestrogens from the mother's milk.

It has been reported that many commercial filters can remove sertraline from blood. For example, commercial Sertraline Filters include the Excel Clean Screen CSXCE106 filter, available from UCT, Inc., 2731 Bartram Rd., Bristol, Pa. 19007 (70% sertraline removal) and the Bond Elut C2 filter, available from Agilent Technologies, 5301 Stevens Creek Blvd., Santa Clara, Calif. 95051. Investigators reported capturing about 95% of sertraline from human plasma using Varian Bond Elut C2 cartridges over a concentration range of 7.5-250 ng/ml. Mandrioli, *J. Chromotography B*, 836 (2006) 116-9. Commercial Ketamine Filters include the Puropher RP-18e filter. Bolze, *Clin. Chem.*, 44, 3, 560-4 (1998) reports capturing about 94-5% ketamine from human plasma with a Puropher RP-18e filter.

Although these commercial filters capture up to 95% of the antidepressant from human blood, it is believed that the blood must first be treated in order to free the 80% of the antidepressant that is bound to plasma proteins. Therefore, it is more accurate to believe that these filters capture up to 95% of the free antidepressant from human blood. Nonetheless, due to the rules equilibrium (which require that the ratio between free and bound antidepressant in blood to be constant), filtration removal of free drug from solution (which lowers the free drug concentration) simultaneously causes a compensating debinding of that drug from the blood's proteins. Many investigators have reported this compensation effect during electrophoretic basic drug removal. See, for example, Ohnishi, *J. Pharm. Biomed. Anal.*, 2002 Jan. 15, 27(3-4) 607-14: "Once unbound (propranolol) migrated apart from lipoprotein, the bound (propranolol) was quickly released from the lipoprotein to maintain the binding equilibrium."; Shibukawa, *J. Pharm. Sci.*, 1994 May, 83(5) 616-9:" The bound drug migrated after it was released from the protein.", and Li, *J. Chromat. Sci.*, 41, March 2003, 137-141: "Because protein binding is a reversible interaction, bound ketoprofen would quickly release from the protein."

Therefore, it is contemplated that the dictates of equilibrium will allow commercial filters to act as a sink for free sertraline that will in turn cause bound sertraline to release from protein. Accordingly, if it is accepted that: a) the free sertraline:bound sertraline ratio in milk is about 20:80, or about 1:4, and b) the free sertraline: trapped sertraline ratio in filter technology ratio is about 1:19 (95%), then, at equilibrium, the trapped sertraline: free sertraline:bound sertraline ratio is about 19:1:4. This means that about 80% of the total sertraline should end up trapped in the filter. This provides a basis for believing that meaningful reductions in sertraline load to the infant can be realized if a filter is used to remove the free sertraline from mother's milk. This also assumes that sufficient time is allowed for the compensation step to free the bound sertraline in the region of the filter;

With reference to FIGS. 1a and 1b, a first embodiment contemplates using a filter to extract sertraline directly from the mother's milk. This embodiment includes:
a) two milk containers 1, which may be plastic or other material, used to store mother's milk, each with a screw top 3, and
b) a fitting 5 that has an intermediate filter 7 and opposed two threaded openings 8,9 that respectively threadably attach to threaded openings 11 on the two milk containers.

The expressed milk from the breast pump is contained in the upper container and is run downward through the filter. The expressed milk passes through the filter, and the milk is thereby cleansed. The filtrate is received in the lower container, such as a milk bottle.

Therefore, there is provided a method of cleaning mother's milk, including the step of: ex vivo contacting mother's milk having an initial concentration of an antidepressant therein with a solid substrate adapted to remove the antidepressant from the milk to produce a cleansed milk product having a reduced concentration of the antidepressant representing a reduction of at least about 10% from the initial concentration of the antidepressant in the mother's milk. The method may further be expanded to a method of providing cleansed milk to a human, and therefore may include the additional step of feeding the cleansed milk product to a human, such as an infant. It is desired that as much of the antidepressant be removed from the milk as practical, and it is understood that some amounts may remain after filtering.

Preferably, the antidepressant removed from the milk includes free antidepressant.

Preferably, the contacting step includes passing the mother's milk through a porous filter.

Also, there is provided an assembly including (a) a vessel having a reservoir; (b) mother's milk contained in the reservoir, wherein the mother's milk has an initial concentration of an antidepressant therein, (c) a solid substrate (preferably a porous solid substrate) contained in the reservoir, the substrate adapted to remove the antidepressant from the milk.

Desirably, the substrate includes a porous filter contained in the reservoir. Preferably, the substrate is attached to the open end of the vessel having an open end and a closed end.

There is also provided a method of cleaning mother's milk, including the steps of: a) passing mother's milk having an initial concentration of an antidepressant therein through a filter to produce a filtrate having a reduced concentration of the antidepressant, and b) feeding the filtrate to an infant.

There is also provided a container for treating mother's milk, including: (a) a first vessel 1 having an open end 31 and a closed end 33, (b) a second vessel 2 having an open end 35 and a closed end 37, and (c) a fitting 5 including: (i) a first endportion 8 adapted for connecting to the open end of the first vessel to provide fluid connection therebetween, (ii) a second endportion 9 adapted for connecting to the open end of the second vessel to provide fluid connection therebetween, (iii) a filter 7 disposed between the first and second endportions of the fitting and adapted for removing an antidepressant from the mother's milk. The first endportion of the fitting connects to the open end of the first vessel to provide fluid connection therebetween and the second endportion of the fitting connects to the open end of the second vessel to provide fluid connection therebetween.

In some aspects, the container further includes: (d) mother's milk 41 disposed in the first vessel, wherein the mother's milk has a concentration of an antidepressant therein. Even further, the container may additionally include (e) a filtrate of the mother's milk disposed in the second vessel, wherein the filtrate has a reduced concentration of the antidepressant. More preferably, the antidepressant has is a lipophilic amine.

Figure 2:
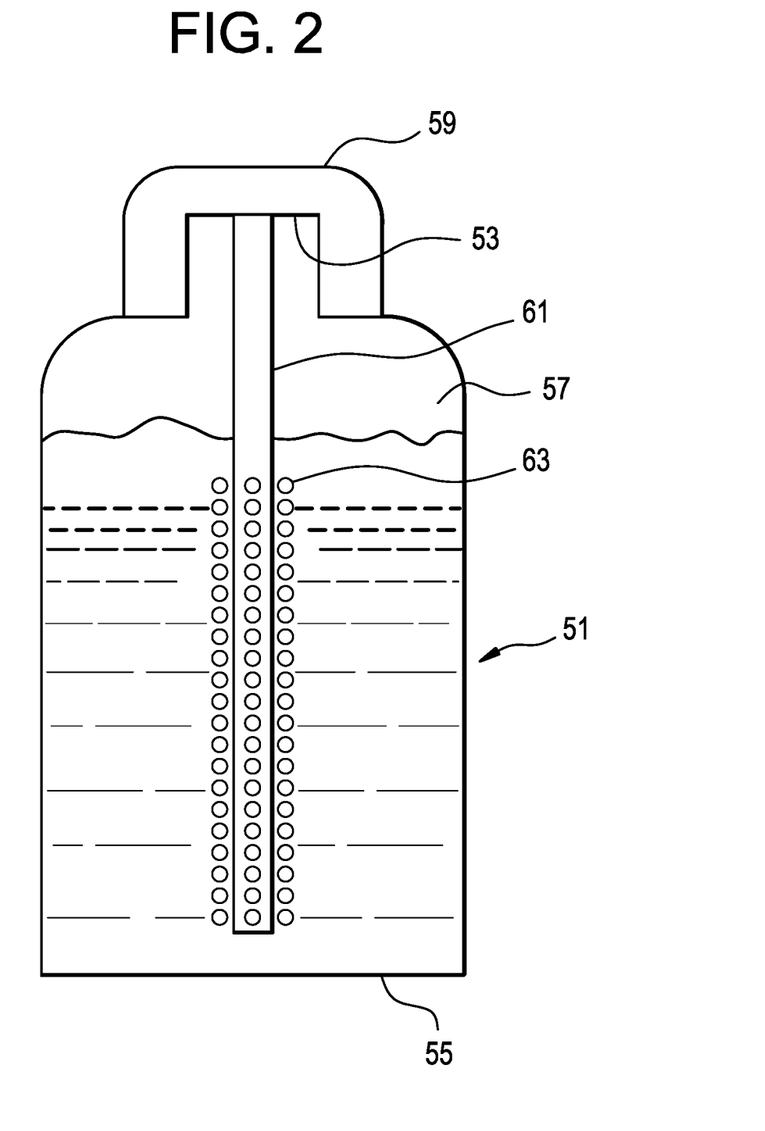
FIG. 2 is a cross-section of an insert extending from the cap into the reservoir, wherein the insert has a substrate adapted to remove the antidepressant from the mother's milk.

In some embodiments, and now referring to FIG. 2, the assembly for removing an antidepressant from mother's milk includes: (a) a vessel 51 having an open end 53, a closed end 55 and a reservoir 57, (b) a cap 59 removably attached to the open end of the vessel, and (c) an insert 61 extending from the cap into the reservoir, wherein the insert has a substrate 63 adapted to remove the antidepressant from the mother's milk. The assembly may further include: (d) mother's milk contained in the reservoir and having a concentration of the antidepressant therein.

Liposome Trapping Technology (LTT)

Figure 3:
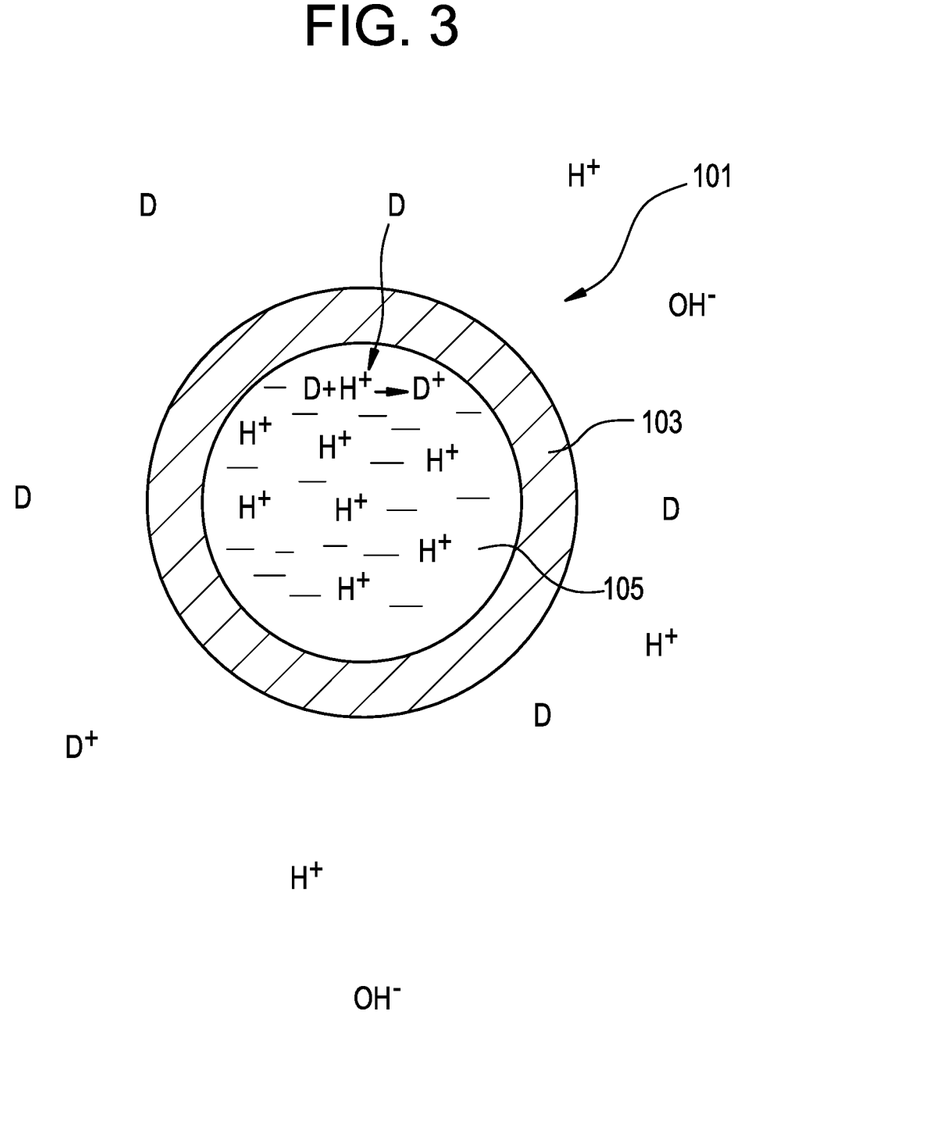
FIG. 3 describes the process by which liposomes with an acid core are able to sequester lipophilic basic drugs by a physicochemical process known as Liposomal Trapping Technology (LTT).

Now referring to FIG. 3, a liposome is a spherical vessel 101 having a lipid bilayer 103 and a core 105. re liposomes are able to sequester drugs by a physicochemical (nonenzymatic, non-transporter-mediated) process known as liposomal trapping. The targets of sequestration are typically lipophilic and amphiphilic drugs [also known as cationic amphiphilic drugs (CADS)], and their propensity to be sequestered (trapped) in liposomes is dictated by their physicochemical properties. Many central nervous system and cardiovascular drugs are lipophilic amines (log P>1) with ionizable amine groups ($pK_a$>6). Such drugs have a neutral fraction at physiologic pH (7.2-7.4) and can readily diffuse across cell membranes by passive diffusion. When such drugs diffuse into liposomes, they become protonated (positively charged) because of the acidic environment of the liposome, which restricts diffusion of drug molecules back across the liposomal membrane into the cytosolic space. The pH partitioning of lipophilic amines into acidic compartments is the mechanistic basis by which these drugs become highly sequestered in liposomes. (Adapted from Kazmi, Drug Metab Dispos., 2013 April; 41(4): 897-905.)

It is believed that lipophilic, basic amine antidepressants such as sertraline and ketamine would be suitable candidates for LTT because they are lipophilic amines (log P>1) with ionizable amine groups ($pK_a$>6). For example, Ketamine has a Log P of 2.18 (and so has a log P>1) and a pKa of 7.5 (and so has a $pK_a$>6). Bissonette, Pediatric Anesthesia, (2011), p. 376, has provided the below Table I estimates of the percentage of ketamine that is in the neutral state at various pHs:

TABLE I

| pH | Fraction of neutral ketamine |
|---|---|
| 7.5 | 50.0% |
| 7.4 | 44.3% |
| 7.1 | 28.0% |

Because Mother's Milk has a pH of about 7.2-7.4, it can be reasonably estimated that there is about a 30-40% neutral fraction of ketamine in milk, this should be a sufficient driving force to utilize LTT. The 30-40% of the ketamine that is neutral in the mother's milk will diffuse into the acidic core of the liposome and become ionized. The ionized form will be trapped in the liposome filter and thereby be removed from the mother's milk.

The above discussion respecting the potential of Liposome Trapping Technology (LTT) is not just theoretical. First, lysosomes present in our liver use a form of LTT to trap drugs. Second, LTT has been used experimentally to filter out drugs. See Yang, *J Chromatogr B Biomed Sci Appl.* 1998 April 10; 707(1-2):131-41." Avidin-biotin immobilization of unilamellar liposomes in gel beads for chromatographic analysis of drug-membrane partitioning." Third, Liposome Trapping Technology is used commercially to make both the DOXIL and MYOCET brands of doxorubicin. Doxorubicin trapping efficiencies using LTT are up to 98% in 60 minutes (37° C.) when using negatively-charged liposomes. Mayer, *Cancer Res.,* 1989, Nov. 1, 49, 21, 5922-30. (Myocet production). Moreover, it has been reported that heating the LTT system drives up removal efficiencies to virtually 100%. Doxorubicin trapping efficiencies using LTT at 60° C. are about 100% in 2 minutes when using negatively-charged (containing cholesterol) liposomes. Mayer, *Cancer Res.,* 1989, Nov. 1, 49, 21, 5922-30.

Therefore, in some embodiments, there is a mild heating of the LTT filter (e.g., between 50° C. and 60° C.) during filtration of the mother's milk. It is believed that such mild heating will not compromise the mother's milk, as milk banks use Holder Pasteurization (60° C. for 30 minutes) to rid donor milk of viruses.

Therefore, in some embodiments, mother's milk passes through a milk-filter system heated up to 60° C. in less than about 2 minutes. In some embodiments, the system is heated to between 45 and 55° C.

In some embodiments, the milk is heated by itself (e.g., on a stove or other heating mechanism). In some embodiments, the filter or fitting may be directly heated. In some embodiments, the milk in the upper vessel is heated.

It is believed that sertraline should be as suitable for LTT trapping as doxorubicin, because its Log P and pKa are similar to doxorubicin, as shown in TABLE II:

TABLE II

|  | Log P | pKa |
| --- | --- | --- |
| Doxorubicin | 1.27 | 9.53 |
| Sertraline | 5.10 | 9.85 |
| LTT requirement | >1 | >6 |

A further advantage of the LTT system is that it appears to be very specific (i.e., it will only remove lipophilic basic amines from the mother's milk). This is important because there are many constituents present in mother's milk that are not available in formula, and which are very beneficial to the child. Some examples thereof include antibiotic proteins and hydroxylated fatty acids such as neuroprotectin. Thus beneficial lipophilic acids (such as docosahexaenoic acid) and hydrophilic basic constituents in mother's milk such as thiamine (log P~−3) will not be captured by LTT.

As with the commercial filters, it is believed that the rules of equilibrium (which dictates that the ratio of bound sertraline to free sertraline remain constant) will allow LTT to act as a sink to cause substantial amounts of bound sertraline/ketamine to be released from milk proteins over time, thus freeing those molecules to be captured by LTT. Since it is believed that: (a) the free sertraline:bound sertraline ratio in milk is 20:80, or 1:4, and (b) the free sertraline: trapped sertraline ratio in liposome technology ratio is 1:99 (LTT efficiency of 99%), then it is conceivable that, at equilibrium, the trapped sertraline: free sertraline: bound sertraline ratio is about 99:1:4. This means that about 95% of the sertraline from mother's milk should end up trapped in the liposomes, provided there is adequate exposure of the milk to a LTT filter.

As shown in Table III, the higher removal efficiency of LTT compared to the commercial filters makes clear that LTT has the opportunity to provide essentially complete removal of the antidepressant from mother's milk.

TABLE III

| Free Sertraline Removal Efficiency | 95% | 99% | 99.9% |
| --- | --- | --- | --- |
| Overall Sertraline Removal Efficiency | 80% | 95% | 99.5% |

Therefore, there is provided a method of cleaning mother's milk, including:
a) ex vivo contacting mother's milk having an initial concentration of an antidepressant therein with a solid substrate adapted to remove the antidepressant from the milk to produce a cleansed milk product having a reduced concentration of the antidepressant, wherein the substrate includes a porous matrix of immobilized liposomes having an acid core.

Preferably, the liposome is negatively charged. Preferably, the mother's milk has a temperature of at least 40° C., more preferably at least 50° C., most preferably at least 55° C. during the contact step.

There may also be provided an assembly including: (a) a vessel having a reservoir; (b) mother's milk contained in the reservoir, wherein the mother's milk has an initial concentration of an antidepressant therein, and (c) a solid substrate contained in the reservoir, the substrate adapted to remove the antidepressant from the milk. The substrate may include a porous matrix of immobilized liposomes having an acid core.

There is also provided a method including: (1) heating to about 60° C. a filter having immobilized cholesterol liposomes with citric acid cores; and (2) allowing mother's milk to pass through the heated filter so that the milk has a residence time therein of about 2 minutes, resulting in an overall antidepressant removal efficiency of at least about 99%.

There is also provided a method of cleaning mother's milk, including the steps of: a) ex vivo contacting mother's milk having an initial concentration of an antidepressant therein with immobilized liposomes having an acidic core to produce a cleansed milk product having a reduced concentration of the antidepressant, and b) feeding the cleansed milk product to an infant.

Preferably, the antidepressant is a lipophilic amine; has a pKa>6 and a log P>1. Preferably, the core of the liposomes has a pH<5; the acidic core of the liposomes includes vinegar or citric acid; and more preferably the acidic core of the liposomes has a pH<4.

It is believed that there are at least four options for immobilizing the liposomes, any of which may be used in the present invention alone or in combination: Avidin-biotin tethering, mucin-pectin mucadhesive tethering, poly-lactic acid polymer (PLLA) coatings on liposomes that are sintered together, and replacement of liposomes with PLLA microspheres that are sintered together. These options are briefly discussed below.

Avidin-Biotin Tethering

Figure 4:
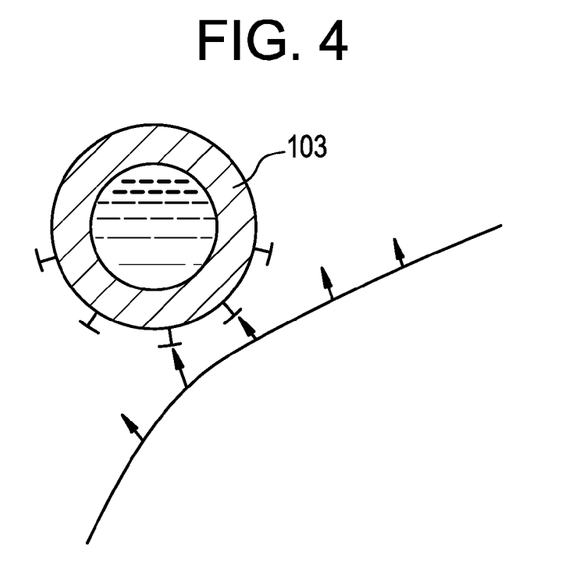
FIG. 4 shows a representation of the avidin (→)/biotin (T) tethering of liposome to a pore in and to an outer surface of a gel bead.

The use of a Avidin-biotin tethering for the immobilization of unilamellar liposomes in gel beads for chromatographic analysis of drug-membrane partitioning is described in Yang, *J Chromatogr B Biomed Sci Appl.* 1998 April 10; 707(1-2):131-41. FIG. 4 shows a representation of the Avidin (→)-biotin (T) tethering of a liposome to a pore in a gel bead, in which biotin is attached to the lipid bilayer 103 of the liposome.

Mucin-Pectin Mucoadhesive Tethering

Figure 5:
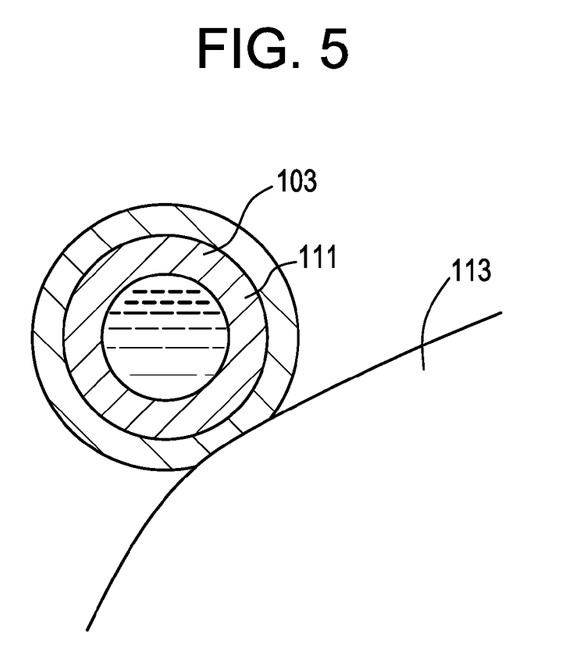
FIG. 5 discloses pectin-coated liposomes immobilized on a surface of a mucin bead.

Now referring to FIG. 5, pectin-coated Liposomes can be Immobilized on and in Mucin beads because pectin 111 and mucin form a mucoadhesive bond. Thus, Liposomes should be present both on the surface of the mucin bead 113 and in the porosity of the mucin bead.

Mucin is a protein found in human milk (Yolken, *J. Clin. Invest.*, 90, November 1992 (1984-91). It is also present in human mucosal layers. Therefore, it is substantially safe for an infant. Investigators have shown that mucin has mucoadhesive properties when combined with pectin-coated liposomes (Klemetsrud, *Colloids Surfaces B: Biointerfaces* 103 (2013) 158-165). Mucin powder is inexpensive (~$50/kg).

The mean pore size of mucin was found to be about 340 nm (Lai, *PNAS,* 107, 2, 598-603, 2010) Because the diameter of the Doxil liposome was found to be 87.3 nm (Soundararajan, *Nucl. Med. Biol.* 2009 July, 36(5) 515-524, it is believed that the DOXIL-like liposomes can easily fit within the porosity of mucin.

Pectin is produced commercially as a white to light brown powder, mainly extracted from citrus fruits, and is used in food as a gelling agent, particularly in jams and jellies. It is also used in fillings, medicines, sweets, as a stabilizer in fruit juices and milk drinks, and as a source of dietary fiber (Wikipedia). Therefore, pectin should be considered to be safe for infants. Pectin powder is inexpensive ($20-50/kg, available from Hunan Arshine Biotechnology). Moreover, it has been reported that pectin-coated liposomes retained their drug trapping ability. (Thirawong, *J. Controlled Release*, 125 (2008) 236-245)

Figure 6:
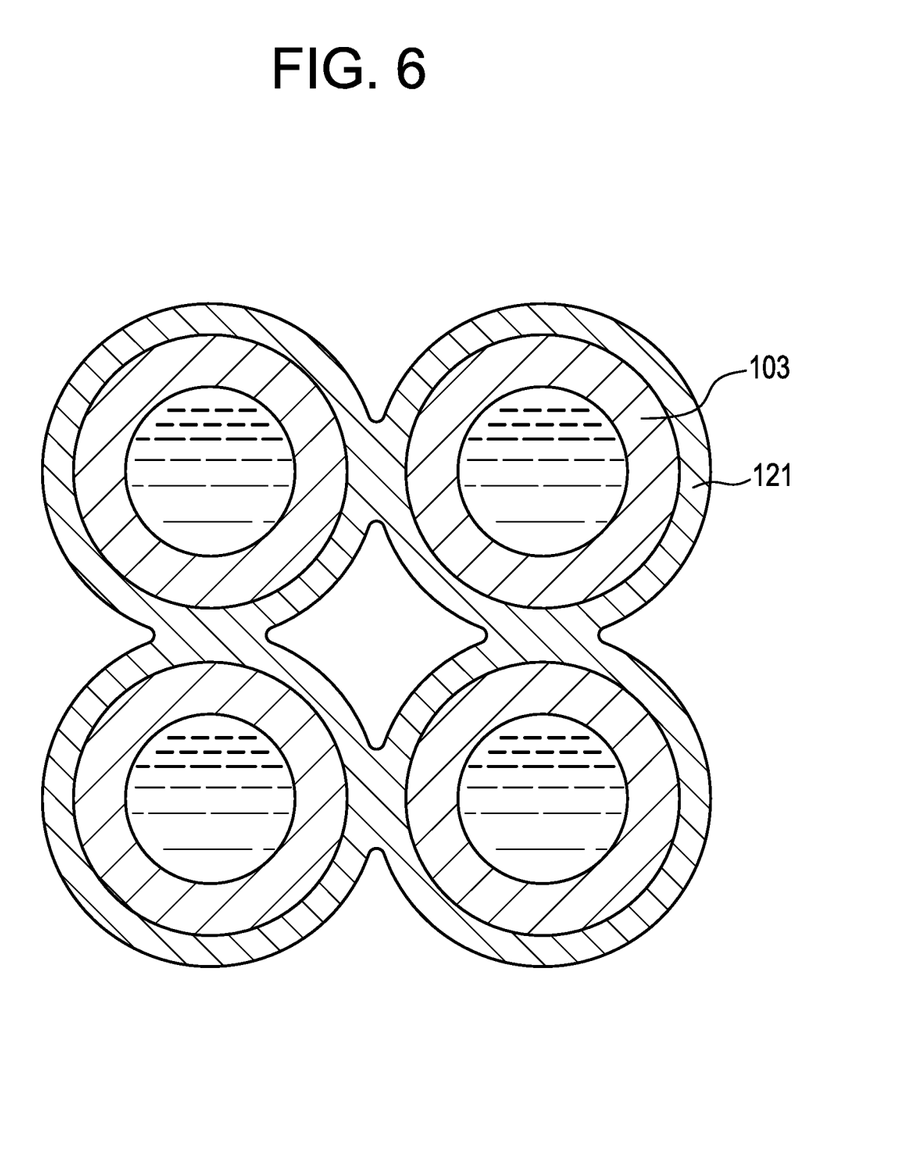
FIG. 6 describes the porous matrix that results when PLLA-coated liposomes that are in contact with one another are heated to the glass transition temperature Tg of PLLA.

Poly-Lactic Acid Polymer (PLLA) Coatings on Liposomes that are Sintered Together PLLA is (L-lactic acid) polymer, an FDA approved implant material that has been used in numerous biomedical applications. The glass transition temperature Tg of PLLA is 59° C. Thus, and now referring to FIG. 6, when PLLA-coated Liposomes that are in contact with one another are heated to the glass transition temperature Tg of PLLA (59° C.), the heat will bond the two liposomes together, thereby producing a "sintered' body that is a porous matrix upon cooling. Subsequent heating of the porous matrix in the milk filtration step may need to stay at or below 55° C. in order to retain the stability of the PLLA matrix 121.

Replace Liposomes with PLLA Microspheres that are Sintered Together

Figure 7:
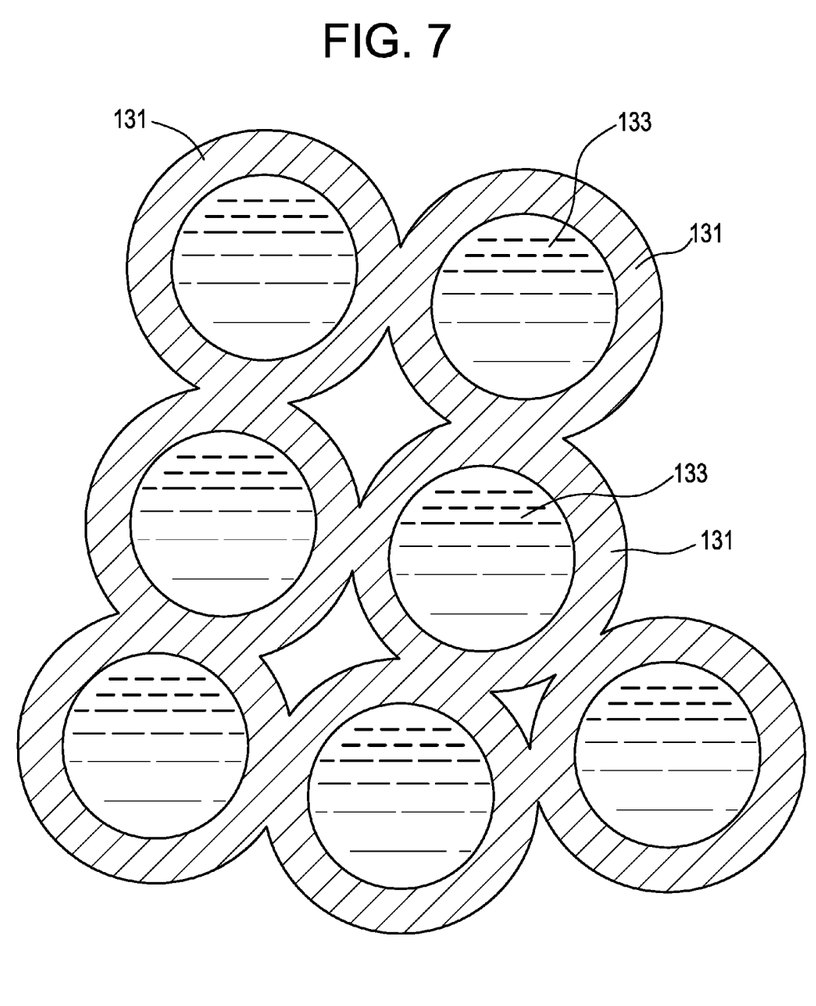
FIG. 7 describes the porous matrix that results when PLLA microcapsules with an acidic aqueous core are heated to the glass transition temperature Tg of PLLA (59° C.).

Conventional microspheres have been used in biomedical situations but typically have a gaseous core due to the porosity in the polymer outer coat. However, recently investigators have succeeded in producing microspheres with aqueous cores. In particular, PLGA microcapsules containing acidic aqueous cores have been developed. Abulateefeh, *AAPS PharmScitech.*, 2015 Sep. 28. Thus, and now referring to FIG. 7, when heated to the glass transition temperature Tg of PLLA (59° C.), PLLA microcapsules 131 with an acidic aqueous core 133 will produce a "sintered" body that is a porous matrix encapsulating acidic aqueous cores. Subsequent heating in filtration step may need to stay at or below about 55° C. to avoid destabilizing the porous matrix.

Therefore, there is provided a method of cleaning mother's milk, including: ex vivo contacting mother's milk having an initial concentration of an antidepressant therein with a solid substrate adapted to remove the antidepressant from the milk to produce a cleansed milk product having a reduced concentration of the antidepressant, wherein the substrate includes a porous matrix selected from the group consisting of: (a) immobilized liposomes having an acid core wherein the liposomes are tethered together via an avidin-biotin tether; (b) pectin-coated liposomes having an acid core immobilized on mucin beads; (c) polymer-coated liposomes having an acid core that are sintered together; and (d) polymer microspheres having an aqueous acid core that are sintered together.

Although filtration is contemplated as a means for antidepressant removal, it is not the only means contemplated. In particular, it is also contemplated that the antidepressant can be removed by simply inserting an insert into a milk bottle, wherein the insert has antidepressant-removing capabilities. An example of this means is shown in FIG. 2.

Thus, there is provided an assembly including: (a) a containing including mother's milk having a threaded opening, and (b) a cap having a threaded opening and an insert extending from the cap that may be assembled with the container, wherein the insert has the immobilized liposomes on its surface.

There is provided an assembly including: (a) a porous matrix including a plurality of immobilized liposomes having an acidic core, and (b) mother's milk present within the porous matrix.

There is also provided an assembly including: (a) a porous matrix including a plurality of microspheres having an acidic core, and (b) mother's milk present within the porous matrix.

Preferably the microspheres are heat-bonded together, preferably at a temperature of at least 55° C.

Figure 8:
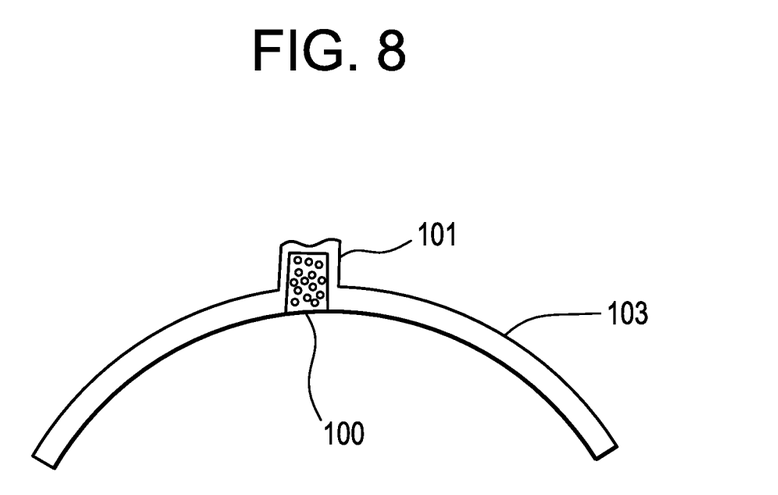
FIG. 8. discloses a filter is incorporated into the nipple of a nipple shield.

In some embodiments, and now referring to FIG. 8, the filter 100 is incorporated into the nipple 101 of a nipple shield 103.

The method of making the liposomes of the present invention can be that substantially described in U.S. Pat. No. 5,616,341 and U.S. Pat. No. 4,898,735, the specifications of which are incorporated by reference in their entireties.

Molecularly Imprinted Solid-Phase Extraction

In some embodiments, the antidepressants are extracted via Molecularly Imprinted Solid-Phase Extraction. Molecularly imprinted filters have been demonstrated to selectively extract Selective Serotonin Reuptake Inhibitors from Untreated Human Plasma. See Sirgom da Silva, "On-Line Restricted Access Molecularly Imprinted Solid-Phase Extraction of Selective Serotonin Reuptake Inhibitors Directly from Untreated Human Plasma Samples Followed by HPLC-UV Analysis", *J Anal Toxicol* (2015 Oct. 20). See also Meng, Anal Chim Acta., 2013 April 10; 771:86-94. doi: 10.1016/j.aca.2013.01.055. Epub 2013 Feb. 8. "Fast screening of ketamine in biological samples based on molecularly imprinted photonic hydrogels."

Therefore, in some embodiments, the filter is a molecularly-imprinted polymer made from an antidepressant, preferably an SSRI, preferably sertraline or paroxetine.

Figure 9:
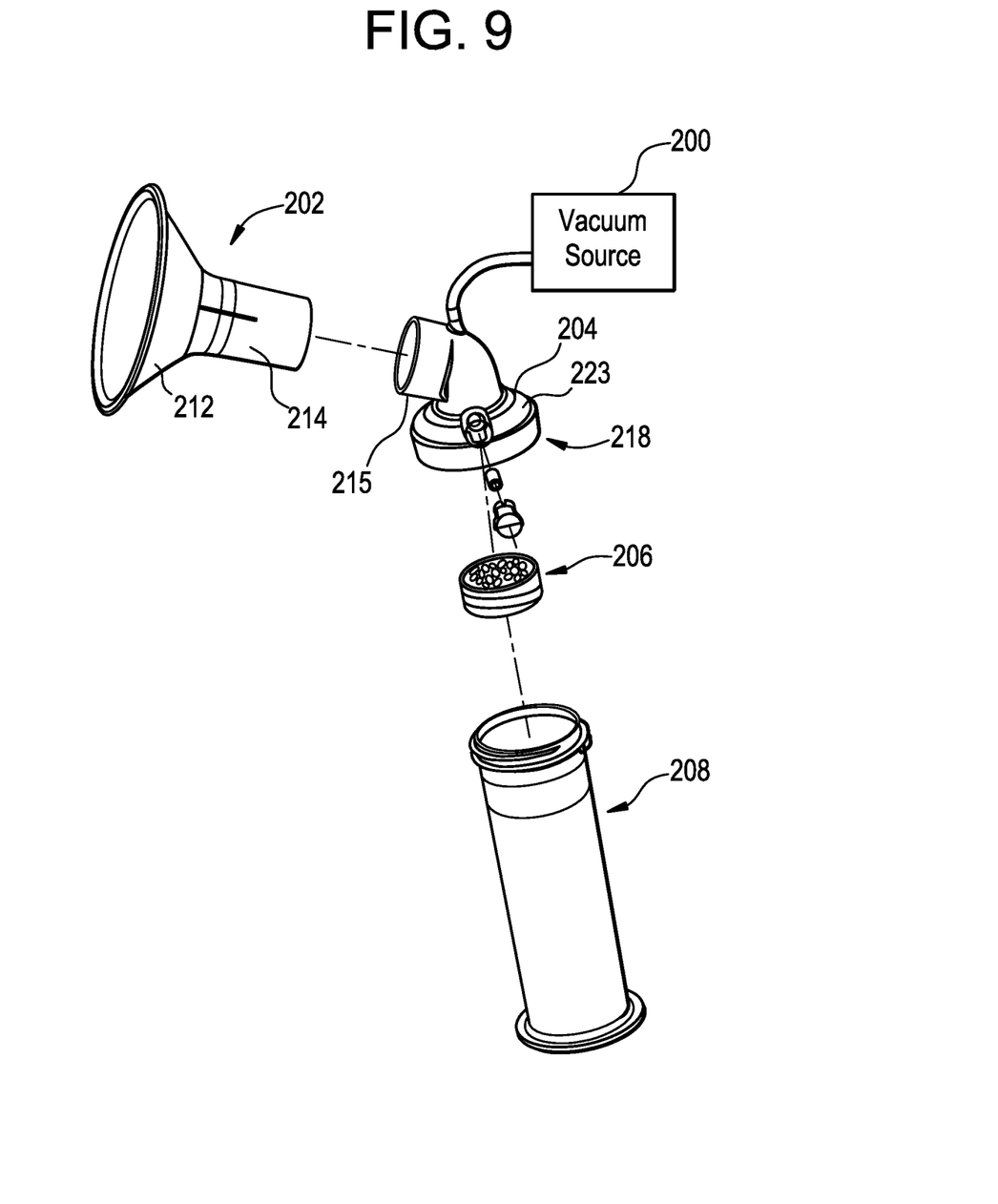
FIG. 9 discloses a filter in a breast pump.

In some embodiments, the filter is provided in a breast pump. Now referring to FIG. 9, there is provided a disposable breast pump assembly including:

a) a breast shield 202 having a first end for placement on a breast and a second end for connection to a collection container;

b) a conduit structure 204 communicating with the breast shield, the conduit structure being in fluid connection with a vacuum source 200 to provide a vacuum function to the breast pump assembly; and c) a filter 206 contained within the conduit structure and adapted for removing an antidepressant from mother's milk.

When used, the breast shield may include a proximal funnel portion 212 adapted for receiving a breast and a distal sleeve 214 adapted for slidable placement within the proximal shield mount 216 of the conduit structure. The conduit structure has a proximal shield mount 216 at the proximal end and a container attachment end 218 at the distal end. A cap 223 is provided within the conduit structure. Filter 206 is placed within the fluid communicating conduit structure so as to be able to filter an antidepressant out of mother's milk passing from the breast shield to the container. In some embodiments, the filter is housed in a threaded annulus that threadably mates with the conduit structure. Container 208 threadably mates with the container attachment end of the conduit structure.

It may be desirable to use a filter system that does not need to be pre-conditioned prior to use. Thus, a method may include the step of passing mother's milk comprising a targeted molecule through a solid phase filter adapted to remove the targeted molecule therefrom without first subjecting the filter to a pre-conditioning step in order to wet the filter.

PET-G

In some embodiments, the porous filter includes a sintered plurality of liquid-filled polymeric microspheres, where at least one microsphere includes a glycol-modified polyethylene terephthalate (PET-G) outer shell and an aqueous core having an acidic pH. The PET-G outer shell may be desirable in some uses, since PET-G has a high Tg (70-110° C.), and also is thought not to leach harmful estrogenic chemicals. Preferably, the PET-G has a Tg of at least 80° C., more preferably at least 90° C., more preferably at least 100° C. The higher Tg embodiments are believed to be more resistant to deformation in instances where the filter is heated. Therefore, liposome trapping technology can be practiced on basic lipophilic molecules at temperatures up to about 60° C. without risking substantial, if any, deformation of the PET-G filter.

Heating

It may be desired to heat milk to aid in filtration. Without wishing to be tied to a theory, raising the temperature of the milk may lower the pKa of a basic target molecule (such as neutral sertraline) therein, thereby providing a greater fraction of the target molecule at neutral pH. The greater fraction of the target molecule enhances that molecule's ability to traverse the hydrophobic vesicles used in liposome trapping technology.

In some embodiments, the milk is heated indirectly by heating the filter or the environment around which the filter is located. This can be accomplished by any desired mechanism, including, for example, by placing resistive heating elements in direct or indirect contact with the filter, or by heating a liquid or solid in direct or indirect contact with the filter. This filter-directed heating embodiment has the additional benefit of essentially only heating the milk during the time that it is within or in contact or in close proximity with the filter, thereby protecting the milk from overheating.

In some embodiments, the energy source that provides the heat is disposed within a milk pump. The energy source is adapted to heat the filter to a predetermined temperature (e.g., between about 50° C. and 60° C.) for a predetermined time (e.g., between two and five minutes).

Removal of Volatiles

In some embodiments, it may be useful to remove volatile components from the milk. The volatile components to be removed may be removed via, for example the energy source discussed above. In some embodiments, the volatile component can be an alcohol such as ethanol. In others, the volatile component can be a sulfur-containing molecule. In others, the volatile component can be a hot pepper-based molecule such as capsaicin or zingerone.

In another aspect of volatile removal, a vacuum is drawn upon the spout of the container holding the milk in order to draw the volatiles out of the milk. In some embodiments, the vacuum source that provides the vacuum is disposed within a milk pump.

It may be useful to incorporate both heating and the use of a vacuum to remove the selected volatile component(s). By using both heat and vacuum, the milk need not necessarily be heated to the same temperature as it would be to remove volatile component(s) without vacuum. This has the advantage of working with a lowered milk temperature to effect volatilization than would be necessary if just heating were used.

In one method, the mother may perform an analysis of the alcohol content of the milk before removal of alcohol (e.g., by heating and/or vacuum) to determine alcohol content in the milk. Further, it may be useful for the mother to perform a second analysis of the alcohol content of the milk after removal of the alcohol (e.g., by heating and/or vacuum) to determine the content within the milk. Alcohol test kits specifically adapted to test for the presence of alcohol in mother's milk, such as the Milkscreen Test Kit for Alcohol in Breast Milk and the Safeguard Easy Use Breastmilk Alcohol Test Strip 20 Pack, are readily commercially available.

Ultrasound

Through the use of filtering, it may be found that desirable endogenous molecules may be inadvertently trapped or retained on the filter after filtration is complete. It may be desirable to include a method of retrieving such desirable molecules, and introducing them back into the filtered milk. In one aspect, ultrasound may be used to remove any such desirable endogenous molecules that may have been inadvertently retained on the filter in order to reintroduce those molecules back into the cleansed mother's milk.

For example, in methods using an strong cation exchange (SCX) filter, there is the chance that thiamine (a quaternary compound) may be inadvertently retained on the SCX filter during and after filtration. It would be desirable to keep thiamine in the filtered milk. Because thiamine is very hydrophilic and even has an anionic functional group, it may be more prone to being released from the filter than is sertraline. The use of ultrasound on a mother's milk filter may allow for removal of inadvertently retained analytes (such as endogenous bases) from the filter and introduce such analytes into the cleansed milk.

Heat Tuning to Reduce Sertraline Loading Time

It is believed that the pKa of a molecule changes with temperature, in particular, that raising the temperature of an aqueous solution containing the molecule decreases the molecule's pKa. For example, where the pKa of caffeine is 14.0 at 25° C., it is only 10.4 at 40° C. Thus, it is believed that raising the temperature of the milk will reduce the pKa of the basic molecules therein and make these basic molecules more amenable for passage into a vesicle of an LTT system. In short, raising the temperature of an aqueous solution containing doxorubicin may decrease the molecule's pKa, thereby increasing the fraction of the molecule that is in a neutral state and augmenting its flux across the lipid bilayer of the liposome. Thus, it is believed that the charged/neutral apportionment of a molecule can be tuned by heating or cooling to suit one's needs.

Heat Tuning to Avoid Endogenous Bases

In some aspects, the target molecule to be removed may have a high pka at room temperature (for example, fluoxetine-Prozac, which has a room temperature pka of about 10.3 and is therefore substantially cationic in substantially neutral milk). If a strong cation exchange (SCX) filter, such as a Phenomenex Strata filter, is used to treat the room temperature milk, then the target drug may be removed. However, it may be useful to consider other endogenous molecules in milk that might also be cationic at a pH of 7 (such as Thiamine, Lysine, Arginine, and Taurine) and thus amenable to inadvertent removal by an SCX filter. That in mind, it may be useful to subject the milk to heat treatment such that the pKa of fluoxetine drops to the pH of milk (e.g., about 7.4). In this aspect, about 50% of the fluoxetine can be cationized and would still be amenable to SCX removal. However, taurine has a pKa of about 9 at room temperature (or about 1.3 units less than fluoxetine) and so taurine may be substantially unionized in the heat treated milk at the higher temperature. Therefore, the heat treating step may result in avoiding retention of taurine on the SCX filter. However, since thiamine is a quaternary molecule (and so is cationic essentially independent of pH), it would not be amenable to tailoring by heat treatment. Therefore, in some heat treating embodiments, taurine may not be retained on the filter, while other molecules, such as thiamine, may be subjected to the filter. In such aspects, additional supplemental steps to recover inadvertently retained molecules may be used to recover such molecules and introduce them back into the filtered milk.

Molecule Replenishment

In some embodiments in which the solid phase filter is a strong cation exchange filter or a weak cation exchange filter, there may be instances in which cationic molecules endogenous to milk might also inadvertently extracted. Some representative examples of these molecules are listed below:

| Milk Cation | pKa | Log P |
|---|---|---|
| Thiamine | 15.5 | −3.1 |
| Taurine | 9.0 | −1.9 |
| Lysine | 9.0 | −3.2 |
| Arginine | 9.0 | −1.7 |
| Histidine | 9.1 | −3.2 |
| Proline | 10.6 | −2.6 |
| Pyridoxine | 8.7 | −0.77 |
| Riboflavin | 10.2 | −0.92 |

In these instances, a method may be used to re-introduce at least one of the aforementioned endogenous molecules back into the milk via supplementation. This is particularly useful when the filter removes one or molecules from the milk that are not intended to be removed from milk, or which is intended to be removed but the user wishes to introduce it back into the filtered milk. In one embodiment, a rod comprising these molecules is provided with the filter system of the present invention to achieve one method. In this method, the mother assesses the height of the column of cleansed milk in the container and breaks the rod at that height so that the length of the rod retained is substantially equal to the height of the column of cleansed milk. This produces a supplementation additive whose quantities of supplements are tailored for the amount of cleansed milk produced.

It is noted that a number of endogenous cationic molecules, including those listed above, are also hydrophilic. As these hydrophilic molecules would have difficulty traversing a lipophilic vesicle such as a liposome, embodiments utilizing LTT (which retains only basic lipophilic molecules) would appear to possess the advantage of selectively avoiding retention of these molecules.

Caffeine

In some embodiments, the mother's milk contains caffeine and the mother desires to remove the caffeine from the milk. In some embodiments thereof, a solid phase filter comprising a molecularly-imprinted polymer adapted to extract caffeine is used. Suitable polymers to extract caffeine include, for example, US Patent Publication No. 2002/0012727, the specification of which is incorporated by reference in its entirety. A filter may be used that includes one or more polymers therein or thereon, which may be used to selectively extract caffeine from the mother's milk. In other embodiments, the caffeine in the mother's milk may be removed via a solid phase filter comprising the dye disodium 3,4,3',4'-bibenzo[b]thiophene-2,2'-disulfonate. This dye may provide for very good retention selectivity over even structurally related analytes.

Other Medications

In some embodiments, medications other than antidepressants may be targeted for removal from the mother's milk. These medications include antipsychotics, anti-epileptics, anti-diabetics and high blood pressure medications. As many of these medications are also basic lipophilic compounds, SCX or LTT filtering technology will likewise be useful in removing these medications from mother's milk.

LTT

In one embodiment, liposome trapping technology (LTT) as described in U.S. Pat. No. 5,736,155, the entire content of which is incorporated by reference herein, may be used as a method of passing a basic molecule from solution, such as milk, through a polymeric or lipophilic shell and into an acidic core.

We claim:

1. A method of cleaning mother's milk, comprising the step of:
   a) ex vivo contacting mother's milk having an initial concentration of an antidepressant therein with a solid substrate adapted to remove free antidepressant from the milk to produce a cleansed milk product having a reduced concentration of the antidepressant representing a reduction of at least 30% from the initial concentration of the antidepressant in the mother's milk, wherein the contacting step comprises contacting mother's milk with immobilized liposomes having an acidic core.

2. The method of claim 1 further comprising the step of:
   b) feeding the cleansed milk product to an infant.

3. The method of claim 2 wherein the contacting step comprises passing the mother's milk through a filter.

4. A method of cleaning mother's milk, comprising the step of: a) passing mother's milk having an initial concentration of an antidepressant therein through a filter to produce a filtrate having a reduced concentration of the antidepressant, wherein the filter comprises immobilized liposomes having an acidic core.

5. The method of claim 4 further comprising the step of: b) feeding the filtrate to an infant.

6. The method of claim 4 wherein the liposome is negatively charged.

7. The method of claim 5 wherein the mother's milk has a temperature of at least 30° C.

8. The method of claim 5 wherein the reduced concentration represents a reduction of at least 30% from the initial concentration of the antidepressant in the mother's milk.

9. A method of cleaning mother's milk, comprising the step of: a) ex vivo contacting mother's milk having an initial concentration of an antidepressant therein with immobilized liposomes having an acidic core to produce a cleansed milk product having a reduced concentration of the antidepressant.

10. The method of claim 9 further comprising the step of: b) feeding the cleansed milk product to an infant.

11. The method of claim 9 wherein the antidepressant has is a lipophilic amine.

12. The method of claim 9 wherein the antidepressant has a pKa >6 and a log P >1.

13. The method of claim 9 wherein the acidic core of the liposomes has a pKa <5.

14. The method of claim 9 wherein the acidic core of the liposomes comprises vinegar.

15. The method of claim 9 wherein the acidic core of the liposomes has a pKa <4.

16. The method of claim 9 wherein the reduced concentration represents a reduction of at least 30% from the initial concentration of the antidepressant in the mother's milk.

17. A method of cleaning mother's milk, comprising the step of: a) passing mother's milk having an initial concentration of an antidepressant therein through a filter to produce a filtrate having a reduced concentration of the antidepressant, wherein the filter is a porous matrix disposed within a breast pump, wherein the porous matrix is selected from the group consisting of:

i) immobilized liposomes having an acid core wherein the liposomes are tethered together via an avidin-biotin tether;
ii) polymer-coated liposomes having an acid core immobilized on mucoadhesive beads;
iii) polymer-coated liposomes having an acid core that are sintered together; and
iv) polymer microspheres having an aqueous acid core.

18. The method of claim 17 wherein the antidepressant is a Selective Serotonin Reuptake Inhibitor.

* * * * *